United States Patent [19]

Hashimoto

[11] Patent Number: 4,961,541

[45] Date of Patent: Oct. 9, 1990

[54] APPARATUS FOR DISPOSING OF A USED HYPODERMIC SYRINGE

[75] Inventor: Teiji Hashimoto, Kanagawa, Japan

[73] Assignee: Kabushiki Kaisha Fuso, Yokohama, Japan

[21] Appl. No.: 401,782

[22] Filed: Sep. 1, 1989

[51] Int. Cl.⁵ .................. B02C 19/12; B02C 19/18
[52] U.S. Cl. .......................................... 241/65; 83/167;
    83/170; 219/68; 241/37.5; 241/99; 241/236
[58] Field of Search ............... 241/65, 66, 37.5, 236,
    241/99, 23, 101.2; 219/68; 128/303.18;
    29/426.4; 83/170, 167; 225/93, 97

[56] References Cited

U.S. PATENT DOCUMENTS

| | | | |
|---|---|---|---|
| 2,101,700 | 12/1937 | Chesnut, Jr. | 241/236 X |
| 3,750,966 | 8/1973 | Anderson | 241/99 |
| 3,929,295 | 12/1975 | Montalbano | 241/99 X |
| 4,628,169 | 12/1986 | Lung | 241/99 X |

FOREIGN PATENT DOCUMENTS 445386  6/1927  Fed. Rep. of Germany ........ 241/65

Primary Examiner—Joseph M. Gorski
Attorney, Agent, or Firm—Oblon, Spivak, McClelland, Maier & Neustadt

[57] ABSTRACT

A used hypodermic syringe disposal apparatus is disclosed which is capable of disposing of used syringes so as to render re-use impossible and prevent possible infection resulting from the used syringes during the disposal operation. A pair of collapsing gears are arranged at a position which permits the gears to be meshed together in such a manner to prevent direct contacting between teeth of the gears. A voltage is applied to the gear while insulation is provided between both gears. When the used syringe is thrown into the apparatus, a hypodermic needle attached to the syringe is burnt immediately upon the needle contacting both gears so as to make them short-circuit. Also, a narrow gap is defined between the corresponding teeth of the synchronously rotating collapsing gears so that a syringe barrel may be effectively crushed in the gap while being transferred between the gears.

4 Claims, 2 Drawing Sheets

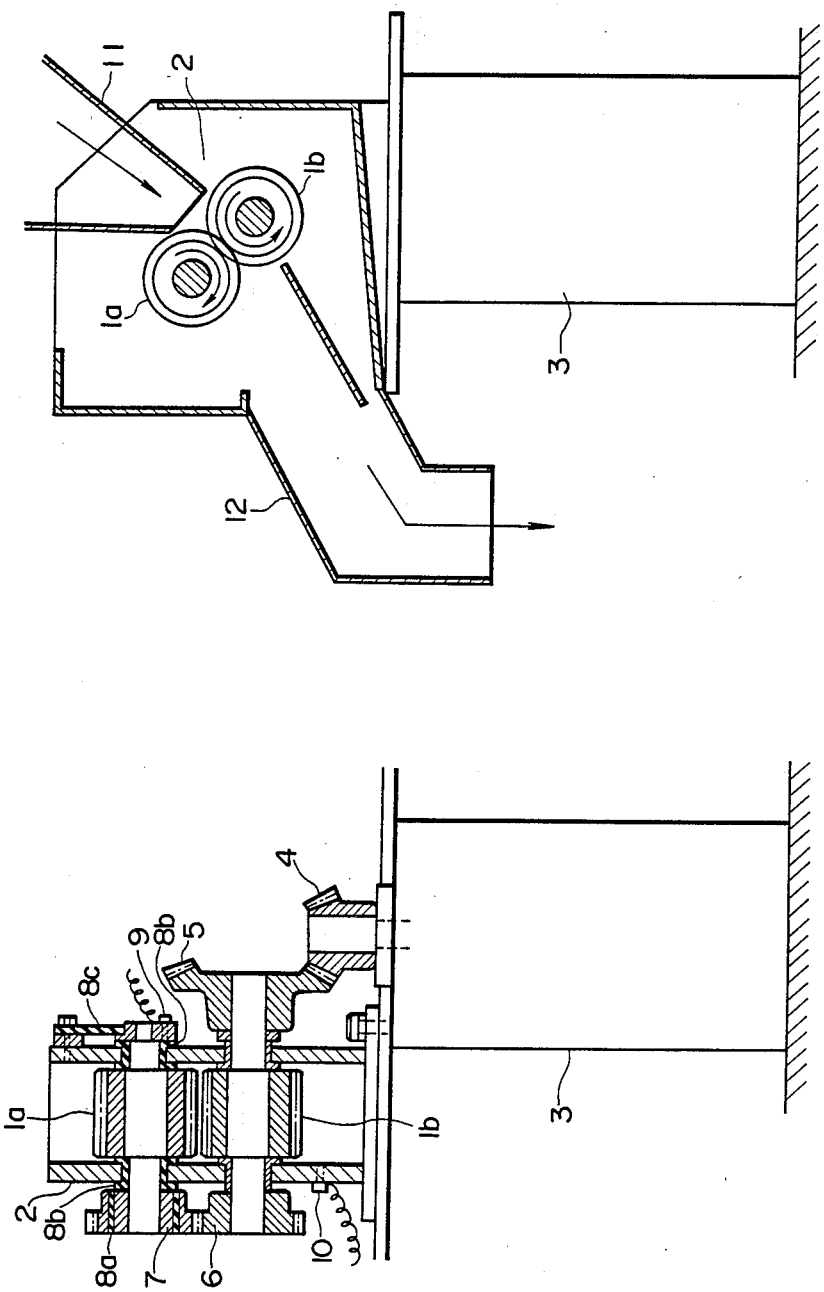

APPARATUS FOR DISPOSING OF A USED HYPODERMIC SYRINGE

BACKGROUND OF THE INVENTION

1. Field of the Invention

This invention relates to an apparatus for disposing of a used hypodermic syringe, and more particularly to an apparatus for crushing a used hypodermic syringe so as to render its re-use impossible.

2. Description of the Prior Art

Recently, a disposable hypodermic syringe and a transfusion liquid container, attached to a hypodermic needle, are generally used in a medical institution, such as, a hospital and a clinic. Thus, a large number of used hypodermic syringes are thrown away everyday from the hospital, which creates serious hygienic problems.

The hypodermic syringe thrown away after use causes infection of a virus disease, such as, B-type hepatitis, acquired immunodeficiency syndrome (AIDS) and the like, if it is re-used or accidentally sticks a doctor's, a nurse's, or a garbage man's skin. In order to prevent such an infection and also a drug abuser from picking up or stealing the used hypodermic syringe for its re-use, the used hypodermic syringe should be disposed so that it cannot be used again.

A conventional used hypodermic syringe disposal apparatus is formed of a crusher which includes rotary cutters engaging with each other. Therefore, the conventional syringe dispoal apparatus is large in size and heavy in weight, and the manufacturing costs become expensive. In addition, it generates a large noise during its operation, because it breaks both the syringe barrel and needle to fine pieces by strong rotating force of the rotary cutters which are directly meshed together. Thus, it is not suitable for use in a doctor's office and like which must be kept quiet.

SUMMARY OF THE INVENTION

The present invention has been made in view of the foregoing disadvantages of the prior art.

It is an object of the present invention to provide an apparatus for disposing of a used hypodermic syringe which is capable of breaking, crushing and/or melting down the used syringe so as to render its re use totally impossible and ensure the safe and hygienic disposal of the used syringe.

In accordance with the present invention, an apparatus for disposing a used syringe is provided. The disposal apparatus includes a pair of collapsing gears arranged at a position which permits the gears to be meshed together, while the teeth of the gears are not directly contacted with each other. The collapsing gears are synchronously rotated, and a voltage is applied thereto, while ensuring insulation between both gears. Thus, when the hypodermic syringe attached to a needle is put into the apparatus to make contact with the collapsing gears together, the gears are short-circuited by the hypodermic needle, which results in melting down the needle due to current passing therethrough, and then the syringe is crushed between the rotating collapsing gears, and discharged to a downward chute.

BRIEF DESCRIPTION OF THE DRAWINGS

These and other objects and many of the attendant advantages of the present invention will be readily appreciated as the same becomes better understood by reference to the following detailed description when considered in connection with the accompanying drawings in which like reference numerals designate like or corresponding parts throughout; wherein:

FIG. 1 is a front elevational view partly in section showing a general structure of an apparatus for disposing of a used hypodermic sryinge according to the present invention;

FIG. 2 is a side elevational view partly in section of the apparatus shown in FIG. 1;

DESCRIPTION OF THE PREFERRED EMBODIMENT

Now, an apparatus for disposing a used hypodermic syringe according to the present invention will be described hereinafter with reference to the accompanying drawings.

An apparatus for disposing of a used hypodermic syringe shown in FIGS. 1 and 2 includes a gear case 2 in which a pair of collapsing gears $1a$ and $1b$ are supported by means of shafts. The collapsing gears $1a$ and $1b$ are synchronously rotated by a motor (not shown) mounted in a casing 3, the driving power of which is transmitted to the collapsing gears $1a$ and $1b$ by means of gears 4, 5, 6 and 7.

Figure 3:
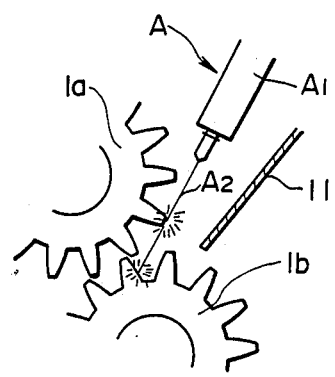
FIG. 3 is a schematic view showing concurrent contact of a hypodermic needle attached to the syringe with both collapsing gears to make short-circuit both gears.

The collapsing gears $1a$ and $1b$ are arranged at a position which permits teeth of both gears $1a$ and $1b$ to be engaged with each other so as not to contact the teeth of the gears $1a$ and $1b$ directly during the rotation thereby maintaining a gap between each of the corresponding teeth. For this purpose, the teeth of the collapsing gears each may be formed into a relatively sharp shape by cutting both the tip ends thereof as shown in FIG. 3. This construction effectively prevents direct contact between the teeth, and ensures rotation of both gears while keeping both gears in position to be meshed together, while maintaing the gap between the teeth which is sufficient to crush the hypodermic syringe between both gears during the rotation.

The apparatus also includes insulating bushes $8a$, $8b$ and $8c$ provided on the side of at least one of the collapsing gears $1a$ and $1b$. In the embodiment shown in FIG. 1, these bushes are provided on the side of the gear $1a$ to insulate the gear $1a$ from the gear $1b$. To the collapsing gear $1a$ is applied a voltage of, for example, about 10 to 40 V through a terminal 9, while the gear $1b$ is earthed by connecting a terminal 10 to the gear case 2 of the apparatus.

Figure 4:
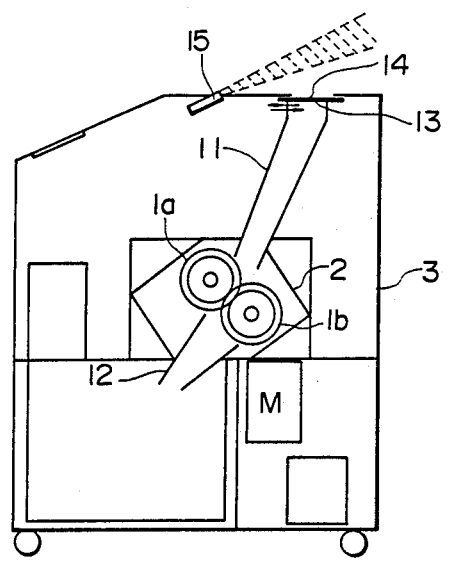
FIG. 4 is a schematic side elevation view showing the apparatus of FIG. 1 provided with a shutter and a sensor device.

As shown in FIG. 4, a shutter 14, such as, a slide door or the like, may be arranged near a charging opening 13 of a chute 11 as well as a sensor 15, such as, a phtosensor arranged in proximity to the shutter 14. Any conventional sensors, such as an approach responsible sensor or a contact responsible sensor may be used for this purpose. In the embodiment shown in FIG. 4, a photosensor is provided in proximity to the shutter 14. The photosensor 15 is arranged so as to emit light beams upwardly at a predetermined angle and width. When the light beams emitting from the photosensor 15 are intercepted by a hand which holds the used hypodermic syringe for throwing it into the apparatus, the photosensor 15 detects the interception and actuates a relay, which is, in turn, to actuate, for example, a solenoid switch, thereby to open the shutter 14. When the used syringe is thrown into the apparatus and the hand retracts to release the light beams from the interception, the shutter 14 is automatically closed.

Now, the manner of operation of the apparatus for disposing the used syringe of the present invention will be described hereinafter with reference to FIG. 3.

When a used hypodermic syringe A consisting of a syringe barrel $A_1$ and a hypodermic needle $A_2$ is put into the apparatus through the loading chute 11 and reaches the collapsing gears 1a and 1b, the needle $A_2$ is burnt down the moment that the collapsing gears 1a and 1b are short-circuited by the needle $A_2$.

The needle $A_2$ is then almost completely melted down thus losing its original shape. If the needle is thick, it is deformed so as to be partially melted. This makes it impossible to re-use the needle and eliminates the danger of injury caused by the needle which accidentally sticks man's skin. Also, the needle is sterilized at a high temperature when it is burnt so as to ensure safety in handling the needle.

The syringe barrel $A_1$ and burnt needle $A_2$ are then captured between the collapsing gears 1a and 1b by rotation of the gears, and then transferred through the small gap defined between the corresponding teeth of the gears 1a and 1b with rotation of the gears which is carried out in such a manner that teeth of both gears are rotated in proximity to each other without directly contacting together, resulting in the syringe being fully broken and crushed. Subsequently, the syringe is downwardly discharged from the chute 12 and then packed in a waste bag, a waste case or the like, and it is finally thrown away after sealing.

If necessary, a disinfectant may be sprayed onto the syringe during or after the collapsing operation.

As can be seen from the foregoing, the apparatus of the present invention is so constructed that a pair of the collapsing gears are arranged with a particular positional relationship to each other and a voltage is applied to the gear system while keeping insulation between both gears. Accordingly, the hypodermic needle attached to the syringe is burnt immediately upon contacting the needle with both gears to make them short-circuit. Also, the narrow gap is defined between the corresponding teeth of the synchronously rotating collapsing gears so that the syringe barrel may be effectively crushed in the gap. The syringe barrel is generally made of plastic material. Accordingly, the crushing may be fully carried out, which makes it impossible re-use the syringe barrel as well as the hypodermic needle attached to the syringe barrel, because it is burnt, and deformed in the gap between the collapsing gears.

As explained hereinabove, the apparatus of the present invention is simple in structure and includes a smaller number of parts. Accordingly, it is compact and can be placed at any location at which the disposal of the used syringe is required, such as, a doctor's office or a medical examination room. In particular, the apparatus of the present invention is able to transfer the syringe through the gap between the synchronously rotating spaced apart collapsing gears. Thus, noises produced during the disposal operation can be significantly reduced as compared with the conventional apparatus wherein gears are meshed directly with each other, and the apparatus of the present invention can be used in the quiet environment of a doctor's office or the medical examination room.

There is much danger of secondary infection not only during injection, blood collection, but also during throwing the used syringe into the disposal apparatus. In order to avoid such a danger, it is desirable to provide the charging opening of the apparatus with the automatic opening and closing shutter, instead of a manually actuated shutter in view of hygienic safety.

In the present invention, the shutter and the sensor are arranged in the vicinity of the charging opening of the loading chute so that the shutter may be automatically operated by merely approaching a hand holding the used syringe to the charging opening, because the photosensor detects the approach of the hand. As a result, the secondary infection can be effectively prevented.

While a preferred embodiment of the present invention has been described with a certain degree of particularity with reference to the drawings, obvious modifications and variations are possible in the light of the above teachings. It is therefore to be understood that within the scope of the appended claims, the invention may be practiced otherwise than as specifically described.

What is claimed as new and desired to be secured by Letters Patent of the United States is:

1. An apparatus for disposing of a used hypodermic syringe comprising:
   a housing having an opening for charging said hypodermic syringe to be disposed and a chute for discharging said hypodermic syringe after having been disposed;
   a drive motor in said housing;
   first and second collapsing gears synchronously driven by said motor, said collapsing gears being arranged in said housing in a position such that teeth of said gears are meshed together without any direct contact with each other during rotation thereof;
   means for applying a voltage to said first collapsing gear while ensuring insulation between said collapsing gears, wherein said first collapsing gear is provided with an insulating bush for electrically insulating said first collapsing gear from said second collapsing gear such that a hypodermic needle, forming part of said hypodermic syringe, upon being charged into said apparatus from said opening causes said collapsing gears to short-circuit by contacting said needle with said collapsing gears so that said needle is burnt, and said syringe is crushed between said collapsing gears and discharged from said chute.

2. The apparatus for disposing of a used hypodermic syringe as defined in claim 1, wherein each tooth of said collapsing gears is formed into a relatively sharp shape by cutting a tip end thereof.

3. The apparatus for disposing of a used hypodermic syringe as defined in claim 1, wherein said opening is provided with a shutter for opening and closing said opening in response to a throwing motion of said used syringe into said apparatus.

4. The apparatus for disposing of a used hypodermic syringe as defined in claim 3, wherein said shutter is actuated by a sensor which detects said throwing motion of said used syringe into said apparatus.

* * * * *